United States Patent [19]

Hempel

[11] Patent Number: 5,299,723
[45] Date of Patent: Apr. 5, 1994

[54] CONTAMINATION-FREE DENTAL FLOSS DISPENSER

[76] Inventor: Jeffrey D. Hempel, 33710 Santiago Rd., Acton, Calif. 93510

[21] Appl. No.: 945,532

[22] Filed: Sep. 16, 1992

[51] Int. Cl.⁵ .......................................... A61C 15/00
[52] U.S. Cl. ................................ 225/38; 225/42; 225/51; 225/53; 225/82; 225/90
[58] Field of Search ................ 242/137, 137.1, 138; 132/323, 324, 325; 225/6, 38, 42, 53, 77, 82, 90

[56] References Cited

U.S. PATENT DOCUMENTS

| | | | |
|---|---|---|---|
| 191,914 | 6/1877 | Beausoleil | 225/6 |
| 466,426 | 1/1892 | Richtmann | 225/44 |
| 1,455,673 | 5/1923 | Shalek | 242/138 |
| 2,554,526 | 5/1951 | Dembenski | |
| 2,707,782 | 5/1955 | Eby | |
| 2,929,541 | 3/1960 | Castelli et al. | 225/44 |
| 3,489,324 | 1/1970 | Stohl | 225/42 |
| 4,073,419 | 2/1978 | Tarrson et al. | 225/44 |
| 4,655,234 | 4/1987 | Bowden | |
| 4,944,440 | 7/1990 | Fortman | 225/6 |
| 5,016,661 | 5/1991 | Israel et al. | 132/325 |
| 5,076,423 | 12/1991 | Russack | 132/325 |
| 5,160,077 | 11/1992 | Sticklin | 225/42 |

Primary Examiner—Hien H. Phan
Attorney, Agent, or Firm—Poms, Smith Lande & Rose

[57] ABSTRACT

A convenient, contamination-free dental floss dispenser assembly having a housing and at least one roll of dental floss mounted for rotation therein. The housing having a dental floss dispensing orifice and cut-off means for cutting off pieces of the dental floss. The floss being free from engagement with the housing and spaced away by at least one-half inch from the housing when the floss extends from the orifice to the cut-off means. Accordingly, the floss free of retaining means, may be gripped by the fingers without touching or contaminating any other part of the housing. The dispenser may also incorporate a means for securely holding the assembly against movement without engagement of the housing by either hand during the dispensing and cutting off of the floss.

7 Claims, 3 Drawing Sheets

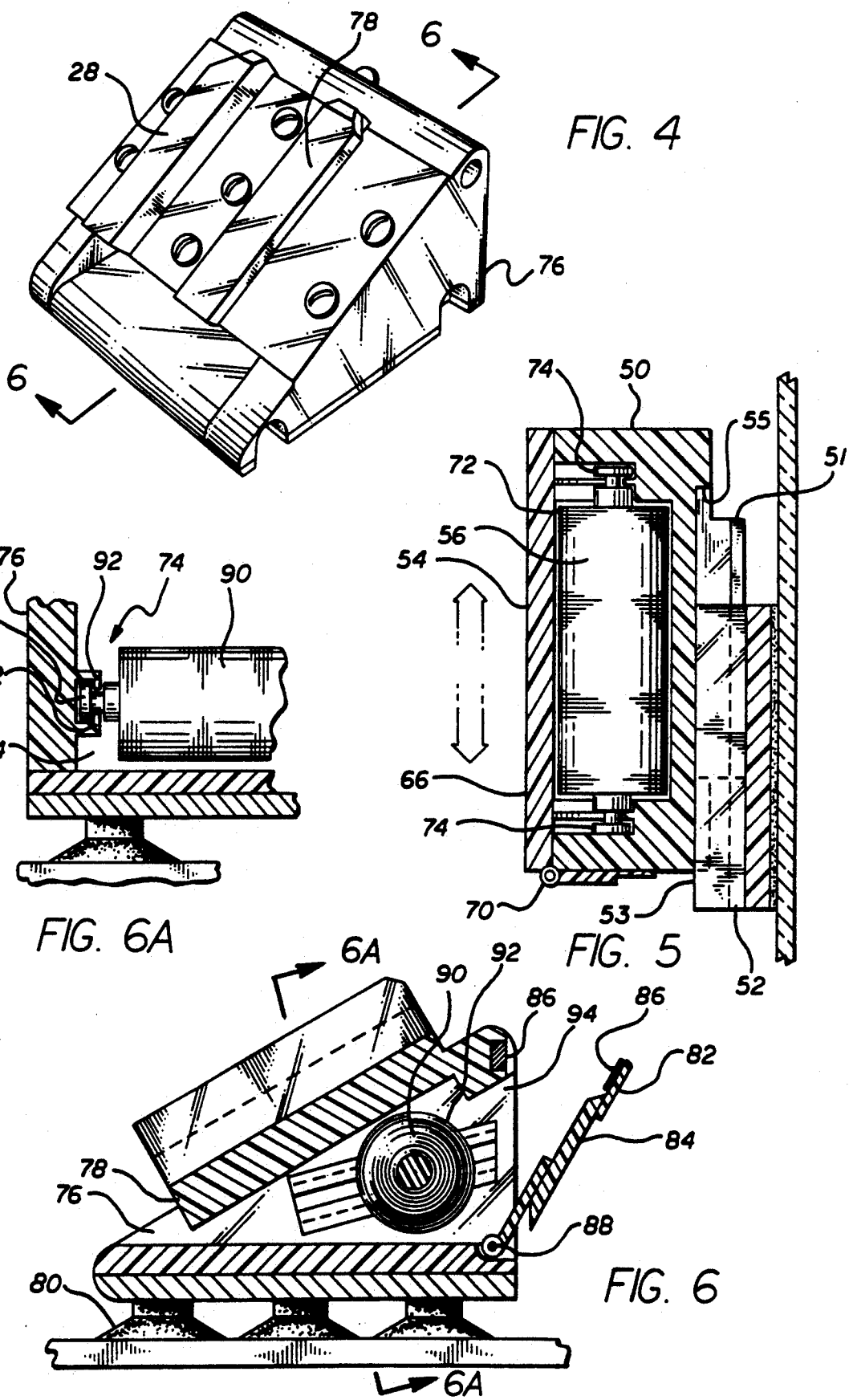

CONTAMINATION-FREE DENTAL FLOSS DISPENSER

FIELD OF THE INVENTION

This invention relates to a dental floss dispenser. More particularly, this invention relates to a contamination-free dental floss dispenser assembly.

BACKGROUND OF THE INVENTION

The flossing of teeth is an integral part of dental hygiene. Whether applied by a dentist or one's self, flossing frequently results in bleeding of the gums. Proper treatment requires the utilization of multiple lengths of floss, thus requiring the practitioner to systematically remove floss from its dispenser. Such a systematic approach may lead to the contamination of the dispenser and the floss contained therein by infectious materials subsisting within the patient's body fluids (i.e. saliva and blood).

Recently the transmission of highly infectious communicable diseases, carried and transmitted through human blood and other body fluids, has received tremendous public attention. Although a myriad of dental floss dispensers are well known, only the present invention provides a practical, economical, and ecological means of preventing the transmission of such diseases through dental flossing.

Two prior art dental floss holders are illustrated in U.S. Pat. Nos. 2,554,526 to Dembenski, and 2,707,782 to Eby. Both of these prior inventions relate to dental floss holders characterized by a housing, encasing a spool of dental floss, from which a pair of fingers extend. The free end of the dental floss may be drawn from the spool and stretched between the free ends of the fingers. The floss is then manually locked into place by wrapping the floss around a post or the like on the housing. Both of these dispensers are operated by forcing the dental floss between adjacent teeth with the long arms of the dispenser extending into the mouth. The user must then manually unlock the floss, draw a new length of floss and lock it into place. This results in the contamination of the newly positioned floss. Further, both of these prior inventions taught an altogether different mode of operation, specifically, the insertion of the extending fingers and the floss running therebetween into the mouth. Such a device would require continued manipulation by the operator and would result in contamination of the housing and the floss therein. Further, neither of these units include arrangements for holding floss in place as floss is dispensed.

It is further noted that dental floss dispensers used by dentists include a variety of table top and hand-held dispensers with a housing, which may be constructed from a variety of materials, encasing the floss. These dispensers generally contained an orifice or slot in the housing permitting the passage of the floss. The user of these units was required to manipulate the floss over a raised cutter mounted in the housing, and the user's fingers would normally engage the housing, and could contaminate the housing and floss. The first slit caught the floss and the second cut it. Contamination is inevitable while operating these dispensers since the user was required to continuously handle the floss and its dispenser with his/her contaminated fingers.

Concerning the use of dental floss at home, the contaminated floss dispenser is normally placed in a drawer or in the medicine cabinet, where it is often forgotten, and not used as often as would be desirable. In addition the floss is not easily drawn out of the dispenser, as the floss lies close to the surface of the container.

SUMMARY OF THE INVENTION

An important object of the invention is to avoid the contamination of dental floss dispensers or the remaining floss. An additional object of the invention is to provide a floss dispenser which is more convenient, appealing and much easier to use than conventional floss dispensers.

According to the present invention, the user needs only to touch the dental floss, thus eliminating the possibility of contaminating either the dispenser or the floss contained therein.

The present invention discloses a contamination-free dental floss dispenser assembly having a housing, at least one roll of dental floss mounted for rotation therein, arrangements for holding the dispenser assembly in place, and fingers extending from the housing providing means for dispensing of the dental floss by gripping the floss between the extending fingers of the dispenser without touching or contaminating the housing or the remaining floss contained therein.

In accordance with one feature of the present invention, a chamber is formed within the housing capable of accommodating at least one roll of dental floss. This chamber may be manufactured to house a variety of dental floss rolls or pre-existing dental floss dispensers. The chamber also incorporates means for mounting the rolls of floss for rotation therein. Through the incorporation of a door on the housing, the floss may be inserted and removed as desired, and once in position the housing may be re-sealed.

In accordance with a further aspect of the present invention, the housing has a dental floss dispensing orifice and a cut-off means for cutting off the desired length of dental floss associated with each roll contained therein. The floss dispensing orifice and cut-off means are located on fingers which extend from the housing. This insures that the floss is spaced away from and free of engagement with the housing. Accordingly, the floss, which is free of retaining means, may be gripped by the fingers without touching or contaminating any other part of the housing or floss contained therein. Of course, the unrolling of the roll of floss and the passage of the floss through the exit orifice provides some slight resistance so that the floss is taut between the orifice and the cut-off point.

Concerning one additional feature of the present invention, the assembly is secured against movement without engagement of the housing by either hand during the dispensing and cutting off of the floss. This is accomplished in a variety of ways including, but not limited to: (1) the inclusion of a weighted base which anchors the assembly; (2) mounting the assembly to a secured structure, counter or a wall by suction cups, or any other fastening arrangements; or (3) the utilization of an adapter, which may be mounted to a wall or secured structure, which is engaged by the assembly, providing means for securely holding the assembly against movement and the added feature of permitting removal of the assembly for cleaning, refilling and/or transporting.

In accordance with another aspect of the invention, the dispenser assembly is free of locking arrangements for the floss as required by the Dembenski and Eby patents. Incidentally, in the present specification and claims, the term "dental floss" is intended to cover all forms of dental floss and dental tape.

When used at home, the floss dispenser assemblies of the present invention have many advantages, including the following:

1. The floss dispenser is easier to use, with the floss easily grasped by the fingers, and with the dispenser mounted in view, rather than hidden in a drawer or in a cabinet.
2. The use of a transparent plastic or other decorator designed floss dispenser makes it more appealing to look at and use.
3. Children will tend to use the floss dispenser to a greater extent with it being in view, particularly if a children's animal or toy design is employed.
4. The capability of refilling the dispensers means they are economical to use.
5. The avoidance of plastic waste when old type dispenser are used up is ecologically desirable.

In summary the present invention provides a host of motivational and health oriented advantages.

Other objects, features, and advantages will become apparent from a consideration of the following detailed description and from the accompanying drawings.

BRIEF DESCRIPTION OF THE DRAWINGS

FIG. 4 is a perspective view of a base capable of storing extra rolls of floss, and having a heavy base and/or suction cups mounted thereon for securing the dispenser against movement as the floss is dispensed;

FIG. 5 is a cross-section view of the contamination-free dental floss dispenser of FIG. 3 with the unit partially inserted on a wall bracket;

FIG. 6 is a cross-section view of the base of FIG. 4 with the door allowing for the insertion and removal of extra spools of floss, ajar;

FIG. 6A is a partial cross-section view taken along line 6a of FIG. 6 illustrating the special ends on the spools of dental floss which may be used in conjunction with the present invention;

DETAILED DESCRIPTION OF THE PREFERRED EMBODIMENT

Figure 1:
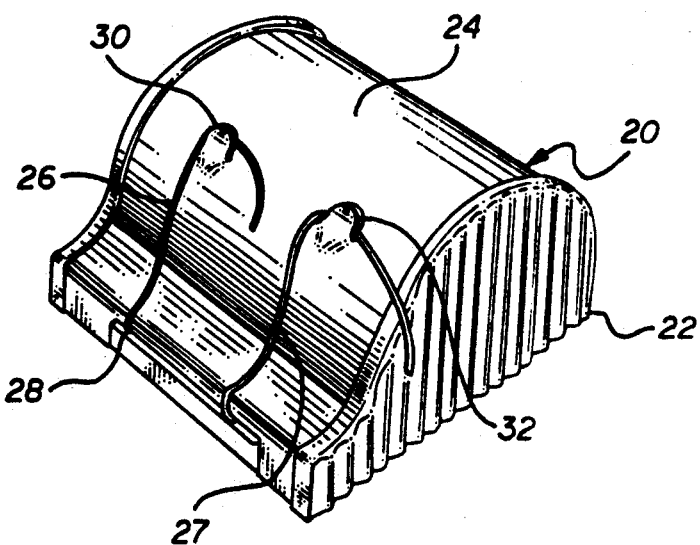
FIG. 1 is a perspective view of a prior art dental floss dispenser.
Figure 2:
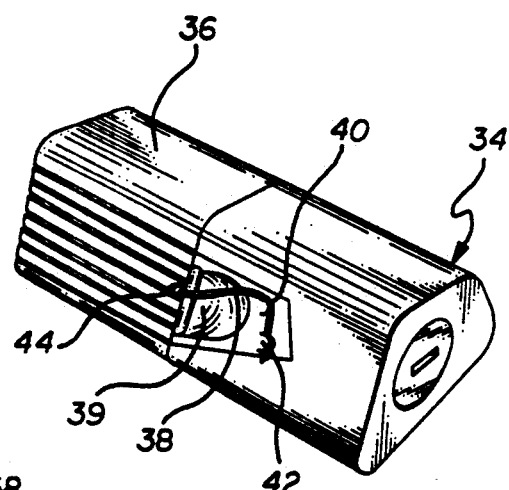
FIG. 2 is a perspective view of another prior art dental floss dispenser.

By way of examples, FIGS. 1 and 2 of the present invention illustrate prior art dental floss dispensers. FIG. 1 represents a table top dispenser 20 with a weighted base 22 and a metal housing 24 encasing two spools, one of the dental floss 26 and the other of dental tape 27. The floss 26 and tape 27 are dispensed through the elongated slot 28 in the housing 24. Its user must manipulate the floss 26 or tape 27 by hand over two raised cutters 30 and 32 in the housing 24. The first cutter 30 cuts the floss 26 and the second 32 cuts the dental tape 27. In use, potentially contaminated fingers engage the housing and in some cases the floss or tape which is not being dispensed.

FIG. 2 is a hand-held dispenser 34 having a plastic container 36 housing the floss 38. The floss 38 is dispensed through an orifice 44 in the container 36, its user must manipulate the floss 38 by hand over two raised cutter slits 40 and 42 on the container 36. A thumb depression 39 is provided to hold the floss as it is cut off, with the entire container being held in one hand while cut off is accomplished by the other hand. The first slit 40 catches the floss 38 and the second 42 cuts it. Neither of these dispensers are suitable to prevent contamination through continued manipulation of the floss and dispenser by a dentist, for example, in repetitively flossing the teeth of successive patients.

While this invention is acceptable of embodiment in many different forms, there is shown in the drawings and will herein be described in detail, a number of embodiments of the invention. The invention disclosed herein is equally applicable to many other shaped and housed dental floss containers besides the embodiments shown and described herein. It should be understood that the present disclosure is to be considered an exemplification of the principles of the invention and is not intended to limit the spirit and scope of the invention and/or claims to the embodiments illustrated.

Figure 3:
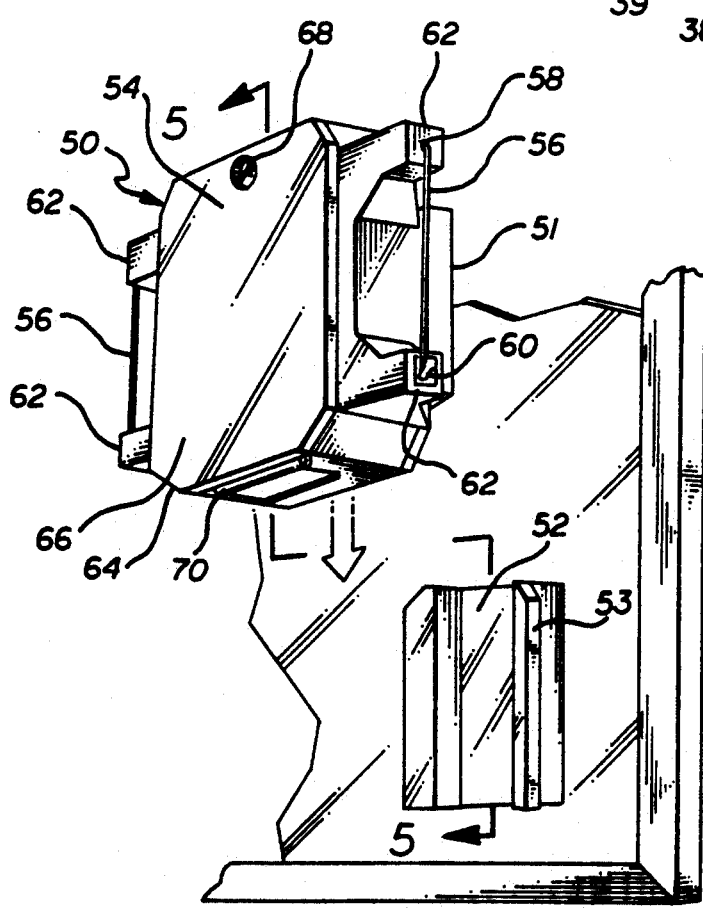
FIG. 3 is a perspective view of a contamination-free dental floss dispenser and its associated adapter for wall mounting shown in the disassembled position, illustrating the principles of this invention.

Referring now to the drawings, FIGS. 3 and 5 illustrate a contamination-free dental floss dispenser assembly 50 having a housing 54, at least one roll of dental floss 56 mounted for rotation therein, arrangements for holding a dispenser assembly in place, and fingers 62 extending from the housing providing means for dispensing of the dental floss 56 without touching or contaminating the housing 54 or the remaining floss 56 contained therein. Further, assembly 50 may be constructed of a variety of materials; however a transparent or translucent plastic material is preferred because it provides added convenience in cleaning the unit and refilling the floss.

Referring now to FIG. 5, formed within the housing 54 is chamber 72 capable of accommodating at least one roll of dental floss 56. The dental floss 56 is mounted for rotation at 74. Various arrangements for mounting the floss are well known in the art and may be incorporated.

Referring back to FIG. 3, a door 66 attached to the housing 54 by hinge 70 provides access to the chamber 72 therein at 64. The door 66 facilitates the insertion and removal of the floss 56. Locking means 68, which may include, but are not limited to a screw or magnets, provide a means of sealing the housing 54 once the floss 56 is in position and protects the floss from contamination by exposure.

Once the floss 56 is in position, it is dispensed through a guide channel and the exit orifice 58. The dispensing orifice 58 located on finger 62 extending from the housing 54, is most preferably located on the finger's distal portion, and is spaced away by at least one-half inch from the housing. Spaced apart from the dispensing orifice 58, and similarly spaced away by a finger 62 extending from the housing 54, is cut-off means 60. This ensures that the floss is free from engagement with the housing. Preferably, each roll of dental floss mounted for rotation within the housing will have its own dispensing orifice and cut-off means. Although the cut-off means 60 may take a variety of forms, preferably a single metallic blade, or a conventional dental floss cutter, may be mounted to the distal portion of the finger 62.

Concerning certain dimensions, it would be desirable for the fingers 62 extending from the housing 54 to provide sufficient space to grip the floss 56 without touching or contaminating the housing or the remaining floss contained therein. This need for sufficient spacing must be counter balanced with the competing interests of structural integrity and manufacturing economy. Accordingly, the fingers 62 should extend from the housing between one-half inch and one and one-half inches (or between 13 mm and 38 mm). Further, the dispensing orifice 58 and cut-off means 60, positioned on the distal portion of the extending fingers 62, are preferably spaced apart from about one and one-half inches to about three inches (or 38 mm to 76 mm).

The assembly 50 is secured against movement without engagement of the housing 54 by either hand during the dispensing and cutting off of the floss 56. Various means of securing the assembly 50 against movement are disclosed herein. This, in cooperation with the above disclosed features, ensures that the floss 56, which is dispensed free of any locking mechanism, may be gripped by the fingers and dispensed without touching or contaminating any part of the housing 54.

One such means of securely holding the assembly 50 against movement is illustrated in FIGS. 3 and 5. Referring now to FIG. 3, an adapter 52 which may be fixed to a wall or a secured object (by various means including but not limited to double-sided adhesive tape, screws or the like) comprises outwardly directed flanges 53 which are engaged by inwardly directed mating flanges 51 of assembly 50 to form a mounting arrangement. As illustrated through FIGS. 3 and 5, the assembly 50 is locked in place by sliding tab members 51 into groove members 53. The downward movement of housing 54 is stopped by the engagement of the flanges 53 against stop surface 55 on housing 54. This arrangement not only provides means of securing the assembly 50 against movement without engagement of the housing 54 by either hand during the dispensing and cutting off of the floss 56 but further allows the assembly 50 to be removed from its secured position for cleaning, refilling and/or transporting to another location where another adapter may be mounted.

Alternatively, the assembly 50 may be secured against movement by adapter 76 which is particularly well suited for table or countertop use. As shown in FIG. 4, adapter 76 may be secured against movement in a variety of ways including mounting the adapter to a table or countertop, incorporating a weighted base, or as illustrated in FIG. 6 through the use of at least one suction cup 80 mounted onto the bottom of the adapter.

Inwardly directed flange members 51 of assembly 50 engage outwardly directed flange members 78 of adapter 76 in a manner substantially the same as that described above with reference to FIGS. 3 and 5. Accordingly, the assembly 50 is locked into place over adapter 76 by interlocking flanges 51 and 78.

A further feature of the table top adapter 76 is illustrated in FIG. 6. This adapter may also store at least one additional roll of dental floss 90 within a chamber 94 which may be opened and resealed at 82. The floss 90 is laterally inserted into the chamber and held in position by retaining means 92. The chamber 94 is sealed by a door 84 which is mounted for rotation by a hinge 88. The door may be locked in place in a variety of ways, including but not limited to a screw or a magnet. FIG. 6 illustrates the magnetic locking means at 86. This arrangement provides contamination-free storage of additional rolls of floss 90 within the adapter 76.

FIG. 6A, a partial cross-sectional view taken along line 6A of FIG. 6, illustrates the present inventor's preferred dental floss mounting assembly 74. The special mating arrangement of assembly 74 is designed to lock the dental floss stored within adapter 76 into position. Assembly 74, which is located within chamber 94, comprises a roll of dental floss having a rounded grooved end 91 which engages tabs 92 in an interfitting arrangement. A similar mounting arrangement is shown at the top and bottom of spool 50 in FIG. 5.

Figure 7:
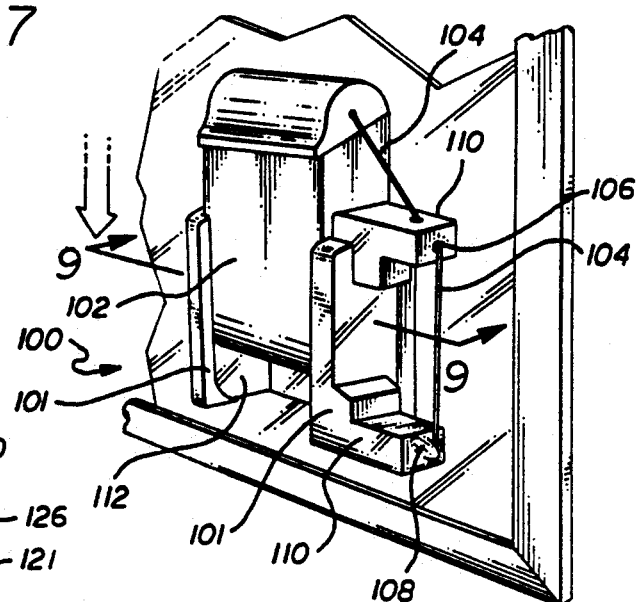
FIG. 7 is a perspective view of a home use unit with a commercially available dental floss box partially inserted.
Figure 9:
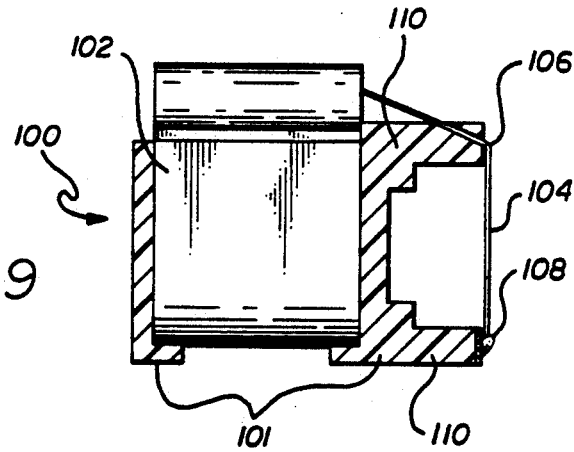
FIG. 9 is a cross-section view through the contamination-free dental floss dispenser of FIG. 7.

One additional embodiment of the present invention, as illustrated in FIGS. 7 and 9, is a home use unit 100 capable of accommodating a pre-existing dental floss dispenser 102. This unit 100 comprises a mount 101 with two side members having recesses 112 capable of accommodating a pre-existing dental floss dispenser 102 which is slid into position. The floss is dispensed free of engagement with any locking mechanisms through dispensing orifice 106, located at the distal portion of finger 110 extending from the housing 101. The floss is stretched from dispensing orifice 106 to the cut-off means 108 which is located on the distal portion of a spaced adjacent finger 110 extending from the mount 101. The home use unit 100 is secured against movement without engagement of the mount 101 by either hand during the dispensing and cutting off of the floss 104 through the use of double sided tape which adheres to the back of unit 100 and to a wall, mirror, countertop, or the like. These features ensure that the floss may be gripped by the fingers and dispensed without any touching or contaminating of any part of the mount 101 or the floss 104 therein.

Figure 8:
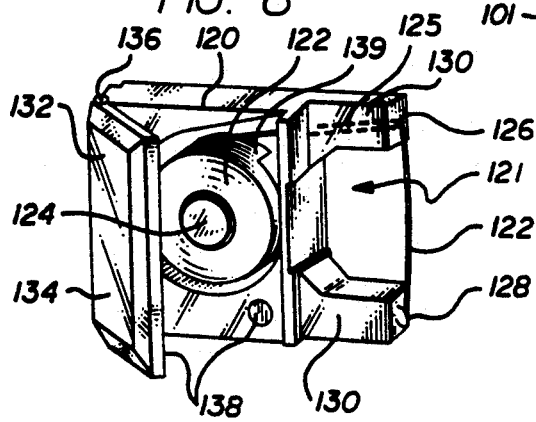
FIG. 8 is a perspective view of a home use unit having a circular roll of dental floss mounted for rotation therein with its door ajar and illustrating a magnetic sealing mechanism.

A further embodiment of the present invention is illustrated in FIG. 8. The home use unit 120 of FIG. 8 comprises a housing 121 having a roll of dental floss 122 mounted for rotation therein at 124. Further, the housing 121 includes a guide channel 125 leading to an exit dispensing orifice 126 and cut-off means 128 both located at the distal portion of fingers 130 extending from the housing 121. The floss 122 is drawn through dispensing orifice 126 without engagement of any locking mechanism. The unit 120 is secured against movement without engagement of the housing 21 by either hand during the dispensing and cutting off of floss 104 through the use of double-sided tape in a manner as mentioned above in the aforementioned examples. Accordingly, the floss may be gripped by the fingers and dispensed without touching or contaminating any part of the housing 121.

The dental floss may be inserted and removed from the chamber 139 of the housing 121 as illustrated in FIG. 8 at 132, through the use of a door 134 which is mounted for rotation to the housing 121 by hinge 136. Chamber 139 may be opened and re-sealed by magnetic closure elements at 138.

Figure 10:
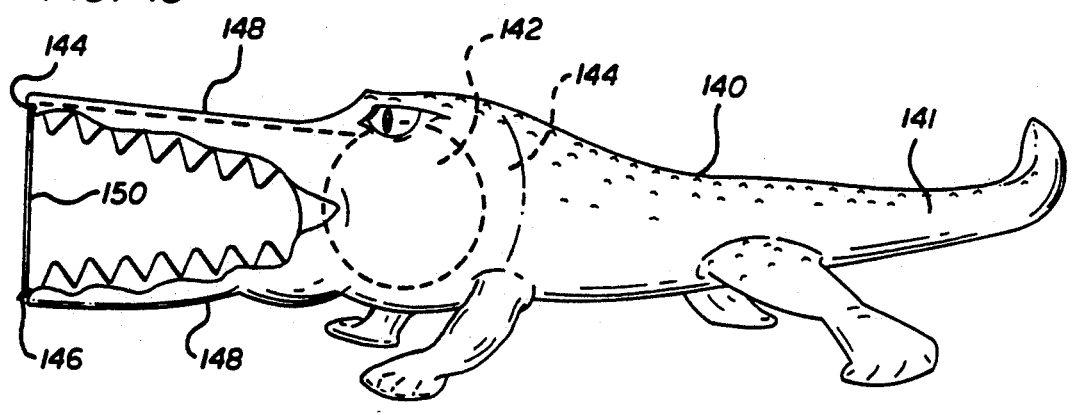
FIG. 10 is a perspective view of a children's unit, illustrating the principles of the present invention.

The units may assume a variety of forms. As illustrated by FIG. 10, such configurations may include a children's unit in the shape of animals or the like having some or all of the features discussed above. The children's unit 140 generally comprises a housing 141 in the form of an alligator having a roll of floss 142 mounted for rotation therein. A dispensing orifice 144 and cutting means 146 are spaced away by fingers or jaws 148 extending from the housing. These fingers 148 which are at least one-half inch in length permit the free dispensing of the floss 142 from the orifice 144 located on the distal portion of the finger 148 without engagement of any locking mechanism so that the floss 142 may be gripped by the fingers and dispensed without touching or contaminating any part of the housing.

While a particular preferred embodiment has been disclosed, it will be understood that variations and modifications may be included without departing from the spirit and scope of this invention. By way of example, but not of limitation, the particular units may assume different configurations or combinations of the features disclosed above, and the magnetic closures could be replaced by other closures or latching mechanisms. It is further noted that, instead of the alligator of FIG. 10, the housing for the dental floss dispenser could be in the form of other figures such as a bird, or Mickey Mouse, or any other desired character. Accordingly, the present invention is not limited to the precise arrangements shown in the drawings and described in detail herein.

I claim:

1. A contamination-free dental floss dispenser assembly comprising:
    a housing;
    at least one roll of dental floss mounted for rotation within said housing;
    said housing having at least one dental floss dispensing orifice and cut-off means for cutting off pieces of said dental floss;
    said floss being free from engagement with said housing and spaced away by at least one-half inch from said housing when said floss extends from said orifice to said cut-off means;
    means for securely holding said assembly against movement without engagement of said housing by either hand during the dispensing and cutting off said floss;
    means for permitting free dispensing of said floss from said orifice without engagement of any locking mechanism so that the floss may be gripped by the fingers and dispensed without any touching or contaminating of any part of said housing;
    said dispenser assembly including at least two thin spaced elongated fingers protruding linearly along a predetermined axis longitudinally directly outwardly from said dispenser at two spaced points, one of said fingers having a dispensing orifice extending through it, and the other having said cut off means attached thereto, said fingers extending separately at least one half inch outwardly from said housing, the maximum cross-sectional dimension through each of said thin, elongated fingers taken transverse to the longitudinal axis thereof, being substantially less than the extent of said fingers away from said housing; and
    a first pair of said thin, elongated fingers extending in one direction from said housing, and second pair of said fingers extending in another direction from said housing.

2. A dental floss dispenser, as defined in claim 1, wherein said housing comprises:
    a chamber for accommodating at least one roll of dental floss;
    means for inserting, removing and sealing said dental floss within said housing; and
    means for mounting said dental floss for rotation within said housing.

3. A dental floss dispenser, as defined in claim 1, wherein said roll of dental floss mounted for rotation within said housing consists of a spool of dental floss which may be easily inserted and removed from said housing.

4. A dental floss dispenser, as defined in claim 1, wherein said means for securely holding said assembly against movement comprises:
    an adaptor attached to a stationary support; and
    said housing having means of engaging said adapter for securely holding said assembly against movement without engagement of said housing by either hand during the dispensing and cutting off of said floss, whereby said assembly may be removed from said adaptor for cleaning, refilling or transporting.

5. A dental floss dispenser, as defined in claim 1, wherein said floss dispensing orifice and said cut-off means are located at the distal portion of the fingers extending directly outwardly from said housing.

6. A dental floss dispenser, as defined in claim 1, having a plurality of rolls of dental floss of different types mounted for rotation within said housing, providing greater versatility in selecting a desired floss.

7. A dental floss dispenser, as defined in claim 1, wherein said fingers extending from said housing extend between one-half inch and one and one-half inches directly outwardly from said housing, and wherein said maximum cross-sectional dimension is less than one-half inch.

* * * * *